(12) United States Patent
Li et al.

(10) Patent No.: US 7,476,403 B2
(45) Date of Patent: Jan. 13, 2009

(54) ORAL EXTENDED-RELEASE COMPOSITION

(75) Inventors: Boyong Li, Morgantown, WV (US); Avinash Nangia, Weston, FL (US); Monte Browder, Plantation, FL (US)

(73) Assignee: Andrx Pharmaceuticals, LLC, Davie, FL (US)

( * ) Notice: Subject to any disclaimer, the term of this patent is extended or adjusted under 35 U.S.C. 154(b) by 548 days.

(21) Appl. No.: 10/869,497

(22) Filed: Jun. 16, 2004

(65) Prior Publication Data

US 2005/0064034 A1    Mar. 24, 2005

Related U.S. Application Data

(60) Provisional application No. 60/478,915, filed on Jun. 16, 2003.

(51) Int. Cl.
- *A61K 9/14* (2006.01)
- *A61K 9/20* (2006.01)
- *A61K 9/22* (2006.01)
- *A61K 9/26* (2006.01)
- *A61K 9/48* (2006.01)
- *A61K 9/52* (2006.01)

(52) U.S. Cl. ............... 424/489; 424/451; 424/457; 424/464; 424/468; 424/470

(58) Field of Classification Search ............... None
See application file for complete search history.

(56) References Cited

U.S. PATENT DOCUMENTS

| | | | |
|---|---|---|---|
| 3,870,790 A | 3/1975 | Lowey et al. | 424/19 |
| 4,064,230 A | 12/1977 | Gordon et al. | 424/459 |
| 5,283,065 A | 2/1994 | Doyon et al. | 424/467 |
| 5,919,489 A | 7/1999 | Saleki-Gerhardt et al. | 424/501 |
| 6,010,718 A * | 1/2000 | Al-Razzak et al. | 424/464 |
| 6,120,803 A * | 9/2000 | Wong et al. | 424/473 |
| 6,340,475 B2 * | 1/2002 | Shell et al. | 424/469 |
| 6,410,054 B1 * | 6/2002 | Thosar et al. | 424/489 |
| 7,063,862 B2 * | 6/2006 | Lin et al. | 424/465 |
| 2003/0044466 A1 | 3/2003 | Markey et al. | 424/469 |
| 2003/0077325 A1 | 4/2003 | Wadhwa | 424/468 |

FOREIGN PATENT DOCUMENTS

| | | |
|---|---|---|
| JP | 60163823 | 8/1985 |
| WO | 9412157 A1 | 6/1994 |
| WO | 9522319 A1 | 8/1995 |
| WO | WO 0059477 A1 * | 10/2000 |

OTHER PUBLICATIONS

Biaxin®, Physician's Desk Reference, (2001) pp. 403-411.

* cited by examiner

*Primary Examiner*—S. Tran
(74) *Attorney, Agent, or Firm*—Hedman & Costigan, P.C.

(57) ABSTRACT

The invention is directed to controlled release formulations containing drugs which are preferably considered sparingly soluble to insoluble and which are suitable for administration to a patient in need of treatment related thereto, and methods of manufacturing the same.

15 Claims, 3 Drawing Sheets

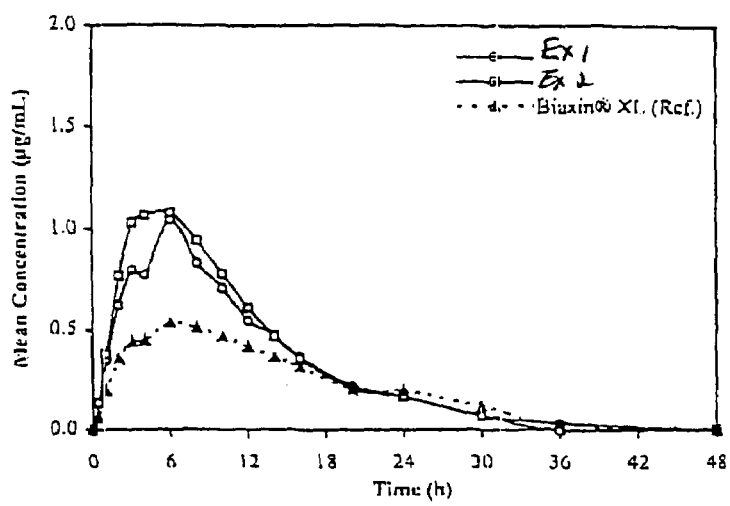
Figure 1. Mean in vivo plasma concentration-time profiles following single dose of one 500 mg Clarithromycin XL tablet under fasting condition.
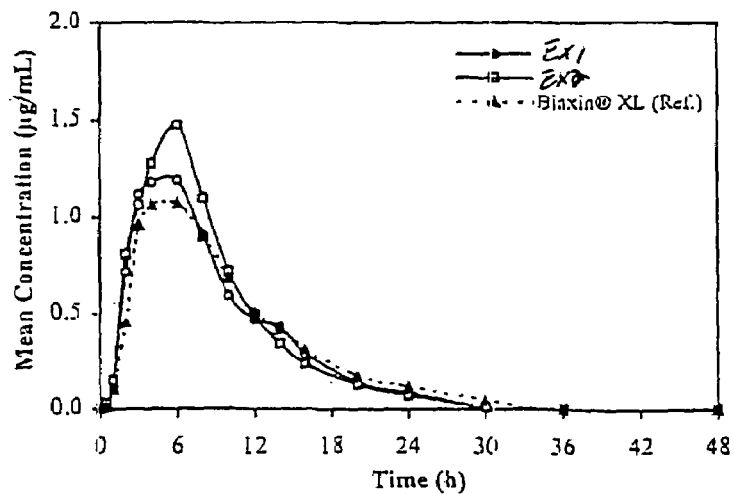
Figure 2. Mean in vivo plasma concentration-time profiles following single dose of one 500 mg Clarithromycin XL tablet under non-fasting condition

ORAL EXTENDED-RELEASE COMPOSITION

This application claims priority of the U.S. Provisional Patent Application No. 60/478,915 filed on Jun. 16, 2003, the disclosure of which is hereby incorporated by reference.

FIELD OF THE INVENTION

The invention is directed to controlled release formulations containing drugs which are considered sparingly soluble to insoluble and which are suitable for administration to a patient in need of treatment related thereto. More specifically, in certain embodiments, the present invention relates to an oral dosage form comprising an erythromycin derivative or a pharmaceutically acceptable salt thereof.

BACKGROUND OF THE INVENTION

It is known in the pharmaceutical art to prepare compositions which provide for controlled release of pharmacologically active substances contained in the compositions after oral administration to humans and animals. Such slow release compositions can be used to delay absorption of a medicament until it has reached certain portions of the alimentary tract. Such sustained-release of a medicament in the alimentary tract further maintains a desired concentration of said medicament in the blood stream for a longer duration than would occur if conventional rapid release dosage forms are administered. Such controlled release dosage forms are believed to lead to improvement in patient therapy.

For example, typical dosing regimens for a class of antibiotics called macrolide antibiotics are two, three or four times per day. These dosing regimens have proved disadvantageous for macrolide antibiotics, as well as other medicaments, because of lack of convenience, and more importantly, lack of compliance. Thus, many techniques have been used to provide controlled and extended-release pharmaceutical dosage forms in order to maintain therapeutic serum levels of medicaments and to minimize the effects of missed doses of drugs cause by a lack of patient compliance.

It is typically the goal of all sustained-release preparations to provide a longer period of pharmacologic response after the administration of the dosage form than that which is ordinarily experienced after the administration of the rapid release dosage forms. However, it is often not possible to readily predict whether a particular sustained release formulation will provide the desired sustained release for a relatively sparingly soluble to insoluble drug, and it has generally been found that it is necessary to carry out considerable experimentation to obtain sustained release formulations of such drugs having the desired bioavailability when ingested.

Generally, it is known that the absorption and bioavailability of any particular therapeutic agent, including sustained release formulations containing therapeutic agents can be affected by numerous factors when dosed orally. Such factorstypically include, but are not limited to, the presence of food in the gastrointestinal (GI) tract. The presence of food in the GI tract usually causes the gastric residence time of a drug to be significantly longer than if administered in the fasted state. If the bioavailability of a drug is affected beyond a certain point due to the presence of food in the GI tract, the drug is said to exhibit a "food effect".

When a drug exhibits an adverse food effect, there is possible risk associated with administering it to a patient who has eaten recently, including but not limited to, the potential that absorption into the bloodstream may be adversely affected to the point that the patient risks insufficient absorption to treat the condition for which the drug was administered. Additionally, drugs which are decomposition-sensitive to pH can be affected as the pH of the stomach varies, between the fed and fasted state, with the amount of food therein. Numerous other factors can also be involved in the absorption and bioavailability of a particular drug, and there usually is no way to predict, in the absence of actual testing, whether a particular drug will exhibit a "food effect". Toothaker and Welling, Ann. Rev. Pharmacol. Toxicol., 1980, 173-99, discuss various drugs whose absorption is delayed in the presence of food (cephalexin, cefaclor, metronidazole, aspirin, alclofenac, indoprofen, digoxin, cimetidine), whose absorption may be unaffected by food (ampicillin, erythromycin estolate, spiramycin, propylthiouracil, oxazepam, bendroflumethiazide), and whose absorption is increased in the presence of food (erythromycin ethylsuccinate, nitrofurantoin, 8-methoxsalen, propranolol, metoprolol, dicoumarol, diazepam, hydrochlorothiazide).

Generally it is known in the art that certain sustained release formulations exhibit a "food effect." Often to avoid such food effect, enteric coatings may be used, allowing the drug to pass through the full (fed) stomach and be absorbed in the intestine. These formulations do not release significant amounts of active ingredient until the dosage form is in the higher pH environment of the small intestine. However, certain active ingredients may have decreased solubility in higher pH's, and are therefore not absorbed well in the intestine.

In view of the aforementioned, there exists a need in the art to provide a controlled release formulation for sparingly soluble to insoluble drugs. In addition, a further need exists to provide a controlled release formulation for sparingly soluble to insoluble drugs which does not exhibit a significant food effect. Accordingly, the present invention provides a novel controlled release formulation comprising a drug which has a solubility of less than about 1 part drug in 30 parts water, which provides for a gradual release of the drug without a substantial or significant fed effect and methods for preparation of the same.

OBJECTS AND SUMMARY OF THE INVENTION

It is an object of certain embodiments of the present invention to provide a sustained release oral composition comprising a drug preferably having a solubility of less than about 1 part drug in 30 parts water and a method of preparation of the same.

It is an object of certain embodiments of the present invention to provide a sustained release oral composition which does not have a significant fed effect and a method of preparation of the same.

It is an object of certain embodiments of the present invention to provide a controlled release form of a macrolide antibiotic which does not have a significant fed effect and a method of preparation of the same.

In accordance with the above-mentioned objects and others, the present invention in certain embodiments is directed to a controlled release solid oral dosage form comprising a multi-granular formulation, preferably a bigranular formulation with one or more drugs in the granulation. Preferably the drug has a water solubility of less than 1 part per 30 parts water. Preferably, the dosage form comprises a first granulation comprising at least one polymer and a drug; a second granulation comprising at least one polymer which is the same or different than the at least one polymer of said first granulation and a drug which is the same or different drug than the drug of the first granulation. Preferably, the first granulation has a faster dissolution rate than the second granulation. In such an embodiment, the release rate of the drug from the dosage form can be modified by adjusting the ratio of the two granulations. Preferably the dosage form provides a mean time to maximum plasma concentration ($T_{max}$) of the drug at from about 1 hour to about 12 hours after administration, more preferably at from about 2 to about 10 hours after administration, and most preferably at from about 2 to about 8 hours after administration.

In certain embodiments of the present invention, the oral dosage form comprises a drug; at least one polymer having a viscosity $V_1$; and at least one polymer having a viscosity $V_2$; wherein $V_1$ and $V_2$ are different. The sustained release dosage form preferably includes a drug having a water solubility of less than about 1 part per 30 parts water. In certain embodiments $V_1$ is less than 50 cps. In certain embodiments $V_2$ is greater than 200 cps. In certain embodiments the dosage form comprises a polymer having a viscosity $V_1$ of less than 50 cps and a polymer having a viscosity $V_2$ greater than 200 cps. In such an embodiment, the release rate of the dosage form can be modified by adjusting the ratio of the low viscosity (e.g., less than 50 cps) and high viscosity (e.g., greater than 200 cps) polymers. Preferably, the dosage form provides a mean time to maximum plasma concentration ($T_{max}$) of the drug at about 1 hour to about 12 hours after administration, more preferably at about 2 to about 10 hours after administration, and most preferably at about 2 to about 8 hours after administration.

In certain embodiments, the invention is directed to a controlled release dosage form comprising at least one drug which is sparingly soluble to insoluble, at least one polymer having a viscosity less than 50 cps, and at least one polymer having a viscosity greater than 200 cps; the dosage form providing a therapeutic effect for at least about 12 hours.

In certain embodiments, the invention is directed to a sustained release oral dosage form comprising a drug having a water solubility of less than about 1 part per 30 parts water and from about 55% or greater by weight of a pharmaceutically acceptable polymer, so that when ingested orally, the composition (a) induces a lower mean fluctuation index in the plasma than an immediate release composition of the drug while maintaining bioavailability substantially equivalent to that of the immediate release composition of the drug, and/or (b) maximum peak concentrations of the drug are lower than those produced by an immediate release pharmaceutical composition, and area under the concentration-time curve and the minimum plasma concentration are substantially equivalent to that of the immediate release pharmaceutical composition.

In certain embodiments, the invention is directed to a sustained release oral dosage form comprising a drug having a water solubility of less than about 1 part per 30 parts water and from about 5 to about 50% or greater by weight of a pharmaceutically acceptable polymer, so that when ingested orally, the formulation does not have a fed effect and (a) the composition induces a lower mean fluctuation index in the plasma than an immediate release composition of the drug while maintaining bioavailability substantially equivalent to that of the immediate release composition of the drug, and/or (b) the minimum plasma concentration are substantially equivalent to that of the immediate release pharmaceutical composition wherein the formulation does not have a fed effect.

In certain embodiments of the present invention, the drug is an antibiotic, preferably a macrolide antibiotic, most preferably erythromycin, an erythromycin derivative, or pharmaceutically acceptable salts thereof. Macrolide antibiotics are typically used for the treatment of a wide range of bacterial infections. The class of macrolide antibiotics are compounds which typically include a 14-membered macrolactone ring and two O-linked sugar molecules. Examples of these compounds useful in the present invention include but are not limited to erythromycin, dirithromycin, josamycin, midecamycin, kitasamycin, tylosin, roxithromycin, rokitamycin, oleandomycin, miocamycin, flurithromycin, rosaramicin, azithromycin, clarithromycin, and pharmaceutically acceptable salts thereof. The macrolide antibiotic, 6-O-methyl-erythromycin A (clarithromycin), is particularly useful in treating common pediatric infections of the middle ear and upper respiratory tract. Other uses of clarithromycin are listed in the 54$^{th}$ Edition of the Physicians' Desk Reference, copyright 2000, pp. 409-417, which is herein incorporated by reference. Clarithromycin is the most preferred macrolide for the present invention and has a solubility of about 1 part in 1,000 parts water.

In other embodiments, the antibiotic is metronidazole or a pharmaceutically acceptable salt thereof.

In certain embodiments where the drug is an antibiotic, the present invention provides a method for treating a microbial infection in a mammal which comprises administering to a mammal that is in need of such treatment, an antimicrobially effective amount of the antibiotic in a controlled release oral dosage form described herein.

In certain embodiments, the present invention is further directed to a method of preparing a controlled release dosage form as described herein.

In certain preferred embodiments of the present invention, the controlled release oral dosage form exhibits substantially no significant food effect when administered to a human patient or other mammal with food.

In certain embodiments of the present invention, the controlled release oral dosage form provides a maximum blood plasma concentration of active drug (Cmax) administered in a fed state which is less than 60% higher or lower than Cmax of said dosage form administered in the fasted state. Preferably the maximum blood plasma concentration of active drug (Cmax) administered in a fed state is less than 50% higher or lower than Cmax of said dosage form administered in the fasted state.

In certain embodiments of the present invention, the controlled release oral dosage form provides a bioavailability based on area under the curve (AUC) when administered in a fed sate which is less than 20% higher or lower than AUC of said dosage form administered in the fasted state. Preferably the bioavailability based on area under the curve (AUC) when administered in a fed state is less than 10% higher or lower than AUC of said dosage form administered in the fasted state.

In certain embodiments, the controlled release oral dosage form is suitable for twice-a-day or once-a-day administration to human patients or other mammal.

In certain embodiments, the dosage form provides therapeutic levels of drug for at least 12 or at least 24 hours.

The term "dosage form" as it is used herein means a dose contained in at least one unit dosage form of the present invention (e.g., the daily dose of the clarithromycin can be contained in 2 unit dosage forms of the present invention for single once-a-day administration).

The term "sustained release" and "controlled release" are used interchangeably in this application and are defined for purposes of the present invention as the release of the drug from the dosage form at such a rate that when a twice-a-day or once-a-day dose of the drug is administered in the sustained release or controlled-release form, blood (e.g., plasma) concentrations (levels) of the drug are maintained within the therapeutic range but below toxic levels over a period of time from about 12 to about 24 hours. When the drug used in the present invention is clarithromycin, the controlled release solid oral dosage form containing such drug may also be referred to as "Clarithromycin Extended Release".

The term "erythromycin derivative" as it is used herein, means erythromycin having no substituent groups, or having conventional substituent groups, in organic synthesis, in place of a hydrogen atom of the hydroxy groups and/or a methyl group of the 3'-dimethylamino group, which is prepared according to the conventional manner, and pharmaceutically acceptable salts thereof.

The term "$C_{max}$" is the highest plasma concentration of the drug attained within the dosing interval, e.g., about 24 hours.

The term "$T_{max}$" is the time period which elapses after administration of the dosage form at which the plasma concentration of the drug attains the highest plasma concentration of drug attained within the dosing interval, e.g., about 24 hours.

The term "$AUC_{0-48}$" as used herein, means area under the plasma concentration-time curve, as calculated by the trapezoidal rule over a complete 48-hour interval.

The term "single dose" means that the human patient has received a single dose of the drug formulation and the drug plasma concentration has not achieved steady state.

The term "multiple dose" means that the human patient has received at least two doses of the drug formulation in accordance with the dosing interval for that formulation (e.g., on a once-a-day basis). Patients who have received multiple doses of the controlled release formulations of the invention may or may not have attained steady state drug plasma levels, as the term multiple dose is defined herein.

The term "mean", when preceding a pharmacokinetic value (e.g. mean $T_{max}$) represents the arithmetic mean value of the pharmacokinetic value taken from a population of patients unless otherwise specified.

The term "fed effect" or "food effect" for the present invention means that when the dosage form is administered in the fed state, at least one of the following occurs:

a. there is a greater than about 20% increase or decrease, in the value for the area under the curve (i.e., AUC) relative to when the dosage form is administered in the fasted state;
  b. there is a greater than about 50% increase or decrease in the value for the maximum blood plasma levels of active drug (i.e., $C_{max}$) relative to when the dosage form is administered in the fasted state; and/or
  c. there is a greater than about 40% increase or decrease in the time to maximum blood plasma concentration of active drug (i.e., $T_{max}$) relative to when the dosage form is administered in the fasted state.

Reference herein and in the claims to a mammal (including humans) that has "eaten" means that the mammal has eaten food (e.g., a high fat meal as defined by the U.S. Food and Drug Administration) within one hour prior to dosing and/or up to two hours after dosing.

The term "bioavailable" is defined for purposes of the present invention as the rate and extent of drug absorbed into systemic circulation from a drug product at its site of administration and which became available at the site of drug action. Bioavailability is usually measured by Area Under (the time-plasma drug concentration) Curve (AUC).

BRIEF DESCRIPTION OF THE DRAWINGS

The following drawings are illustrative of embodiments of the invention and are not meant to limit the scope of the invention.

FIG. 1 is a graph of the mean in vivo plasma concentration-time profiles for Examples 1, 2, and a reference standard, following single dose of one 500 mg Clarithromycin Extended Release Tablet under fasting conditions.

FIG. 2 is a graph of the mean in vivo plasma concentration-time profiles for Examples 1, 2, and a reference standard, following single dose of one 500 mg Clarithromycin Extended Release Tablet under non-fasting or fed conditions.

DETAILED DESCRIPTION OF THE INVENTION

Figure 3:
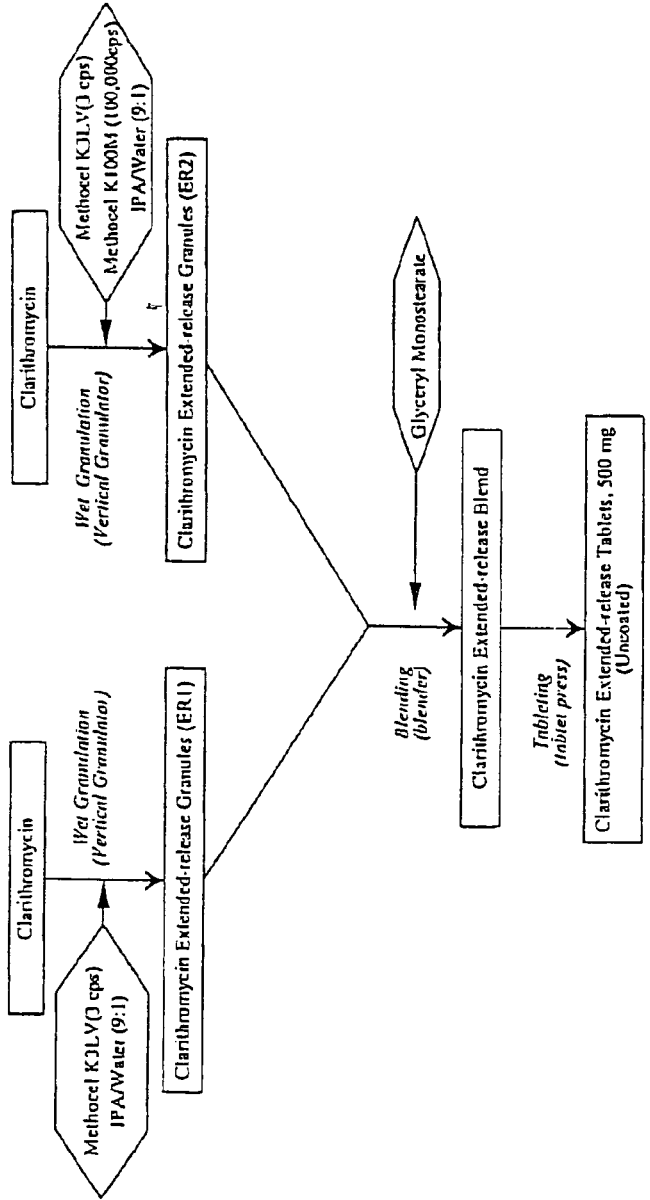
FIG. 3 is a flow chart depicting the manufacturing process for Clarithromycin Extended Release Tablets with 500 mg Clarithromycin.
Figure 4:
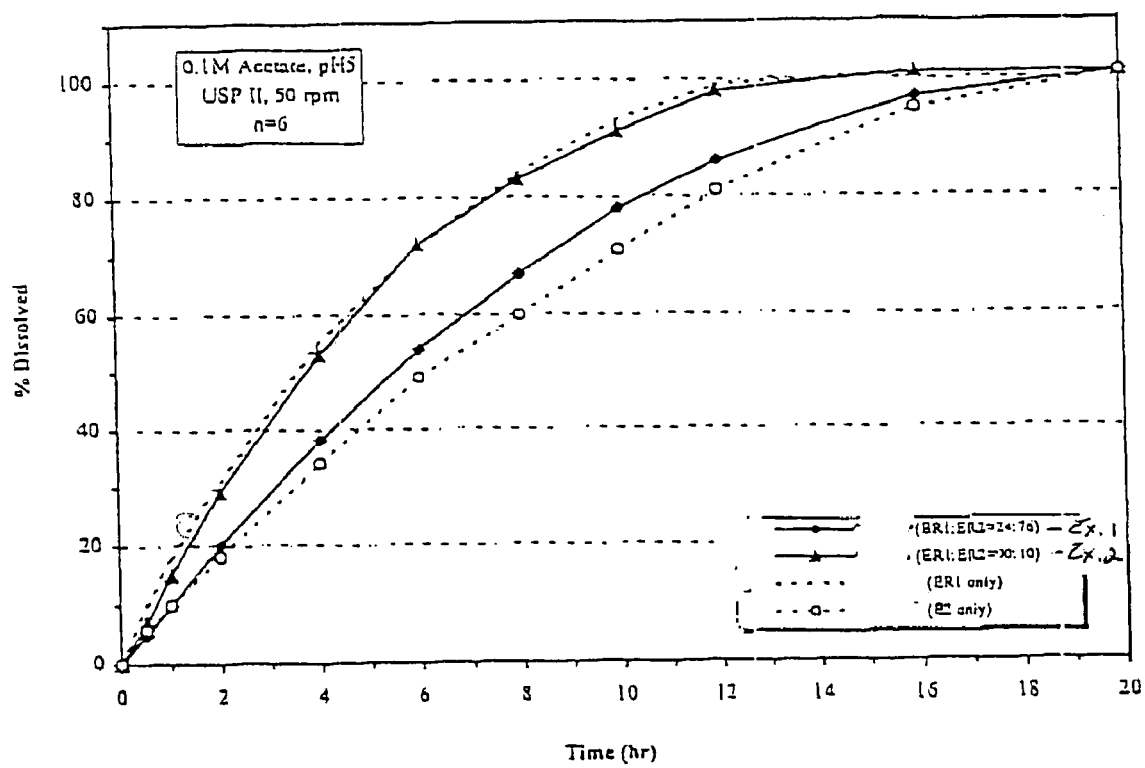
FIG. 4 is a graph of in vitro dissolution data which shows the dissolution profiles of the formulations of Examples 1, 2, the ER 1 Granules separately, and ER 2 Granules, in 0.1M Acetate at pH 5.0 in a USP XXII Type II dissolution apparatus at 50 rpm.

The present invention provides for a controlled release, e.g., once-a-day daily dose regimen for at least one drug, which is preferably considered sparingly soluble to insoluble, to a patient in need of treatment related thereto. More particularly, the present invention provides a controlled release pharmaceutical composition comprising controlled release polymers in order to deliver the drug over an extended period of time. Preferably the composition of the present invention is in tablet or capsule form.

In accordance with the present invention, the drugs useful in the controlled release formulations of the present invention are preferably drugs having a solubility of less than 1 part drug in 30 parts of water. These drugs are defined by the USP/NF 23/18, herein incorporated by reference, as "sparingly soluble" (from 30 to 100 parts of solvent for 1 part of solute); "slightly soluble" (from 100 to 1000 parts of solvent for 1 part of solute); "very slightly soluble" (from 1000 to 10,000 parts of solvent for 1 part of solute); "practically insoluble", or "insoluble" (more than 10,000 parts of solvent for 1 part of solute).

By way of example, drugs useful in accordance with the present invention may include antibiotics such as, for example, sulfamethoxazole with a solubility of 1 in 3,400 (parts of water); tetracycline, 1 in 2,500; metronidazole and cimetidine (a histamine $H_2$ receptor antagonist for treating ulcers), both about 1 in 100 to 1 in 1,000; indapamide (an antihypertensive/diuretic), 1 in more than 10,000; atenolol (an antihypertensive), about 1 in 30 to 1 in 100; diazepam (tranquilizer), ranging from 1 in 1,000 to 1 in 10,000; and the like.

As a preferred drug, the present invention includes an antibiotic, preferably a macrolide antibiotic which preferably has a solubility of less than 1 part drug in 30 parts water. Examples of these compounds useful in the present invention include but are not limited to erythromycin, dirithromycin, josamycin, midecamycin, kitasamycin, tylosin, roxithromycin, rokitamycin, oleandomycin, miocamycin, flurithromycin, rosaramicin, azithromycin, clarithromycin, derivatives thereof, and pharmaceutically acceptable salts thereof.

In certain preferred embodiments of the present invention, the sustained-release oral dosage form of the present invention includes from about 50 to about 1000 mg clarithromycin, and more preferably from about 250 mg to about 500 mg clarithromycin.

In certain other preferred embodiments of the present invention, the sustained-release oral dosage form of the present invention includes from about 100 to about 1500 mg metronidazole, more preferably from about 500 mg to about 1000 mg metronidazole.

In certain embodiments of the present invention, the pharmaceutical composition may include other drugs in combination with a drug having a solubility of less than 1 part drug to 30 parts water. For example, the macrolides erythromycin or clarithromycin may be formulated in combination with a preparation for standard therapy of gastritis, ulcers or gastroesophagal reflux disease (GERD), such as preparations containing anti-ulcer or anti-gastritis medicaments; e.g., omeprazole, cimetidine, ranitidine, lansoprazole, pantoprazole, sucralfate, famotidine, or nizatidine, or antacids such as magnesium hydroxide, aluminum hydroxide, sodium carbonate, sodium hydrogen carbonate, simethicone or aluminum magnesium hydroxide or hydrate thereof (such as the monohydrate known as magaldrate). Additionally, the erythromycin or clarithromycin, pharmaceutical composition of the present invention may be adapted to be administered in combination with a preparation containing bismuth salts such as bismuth subcitrate, bismuth subsalicylate, bismuth subcarbonate, bismuth subnitrate or bismuth subgallate.

The amount of drug or drugs in the pharmaceutical composition may vary from about 1 to 99% of the dosage form, preferably 25 to 75% of the dosage form, most preferably from about 35 to about 65% of the dosage form. For clarithromycin, the amount may preferably vary over 25% and up to about 75% of the weight of the dosage form, preferably from about 30 to about 60% of the weight of the dosage form.

In certain embodiments wherein the present invention comprises a multiple granular composition, each granular composition comprises at least one pharmaceutically acceptable, water swellable polymer or hydrogel. Preferably, the controlled release dosage form comprises a bigranular composition comprising a first granulation and a second granulation wherein the first granulation comprises at least one polymer and a drug and the second granulation comprises at least one polymer which may be the same polymer as the polymer of the first granulation, or a different polymer than the polymer of the first granulation. In addition, the second granulation contains a drug which may be the same drug or a different drug than the drug of the first granulation. In certain preferred embodiments the first granulation has a faster dissolution rate than the dissolution rate of the second granulation, and the release rate of the drug from the dosage form can be modified by adjusting the ratio of two types of granulations.

In certain multi-granular embodiments, the first granulation comprises from about 1% to about 99% of the dosage form; from about 10% to about 90% percent of the dosage form; from about 20% to about 80% of the dosage form or from about 40% to about 60% of the dosage form.

In certain multi-granular embodiments, the second granulation comprises from about 99% to about 1% of the dosage form; from about 90% to about 10% percent of the dosage form; from about 80% to about 20% of the dosage form or from about 60% to about 40% of the dosage form.

In certain multi-granular embodiments, the drug can be completely extragranular, partially extragranular, or completely or partially contained in at least one of the granulations. Preferably, the multi-granular dosage forms do not contain extragranular drug and a portion of the drug is contained in each granular composition (e.g., each granulation contains the same drug).

In certain preferred multi-granular embodiments which do not comprise extragranular drug, the first granulation comprises from about 1 to about 99 percent of the final formulation, and the second granulation comprises from about 99 to about 1 percent of the final formulation. Preferably the first granulation comprises from about 5 to about 90 percent of the final formulation and the second granulation comprises from about 90 to about 5 percent of the final formulation. More preferably the first granulation comprises from about 20 to about 80 percent of the final formulation and the second granulation comprises from about 80 to about 20 percent of the final formulation.

In certain other embodiments, the dosage form comprises a drug preferably having a water solubility of less than 1 part per 30 parts water; at least one polymer having a viscosity $V_1$; and at least one polymer having a viscosity $V_2$; wherein $V_1$ and $V_2$ are different values. Unless otherwise noted, all viscosity values are measurements for an aqueous solution 2% w/w at 20° C. $V_1$ and $V_2$ can have values of from about 1 cps to about 100,000 cps or greater in order to provide for the sustained release of the drug; provided that $V_1$ and $V_2$ are not the same values. In certain embodiments $V_1$ is less than 50 cps and $V_2$ is a cps value other than the $V_1$ value. In certain other embodiments, $V_2$ is greater than 200 cps and $V_1$ is a cps value other than the $V_2$ cps value. In certain preferred embodiments, the dosage form comprises at least one low viscosity polymer having a viscosity less than 50 cps; and at least one high viscosity polymer having a viscosity greater than 200 cps, wherein the release rate of the drug from the dosage form can be modified by adjusting the ratio of the low and high viscosity polymers. The ingredients can be granulated (e.g., wet granulated) to form a single granulation or can be dry mixed prior to being incorporated into a dosage form.

In certain embodiments having a polymer with a viscosity $V_1$ and a polymer with viscosity $V_2$, the polymers are in a weight percentage that provides for the sustained release of the drug in the dosage form. For example, the polymers having a viscosity $V_1$ and $V_2$ may be in an amount of from about 1% to about 99% w/w; from about 10% to about 90% w/w; from about 20% to about 80% w/w or from about 40% to about 60% w/w of the dosage form provided that the combination of the polymers provides for the sustained release of the drug in accordance with the present invention. Preferably the dosage form comprises at least one low viscosity polymer is in a combined amount of less than 5% w/w or greater than 50% w/w of said dosage form. In other embodiments the at least one high viscosity polymer is in a combined amount of less than 5% w/w or greater than 50% w/w of said dosage form. In other embodiments, both the low and the high viscosity polymers are in an amount of less than 5% w/w or greater than 50% w/w of the dosage form.

In preferred embodiments one of the low and high viscosity polymers is in an amount 50% w/w or greater of the dosage form. In such embodiments, the combined amounts of the low and high viscosity polymers is e.g., about 55% w/w or greater, about 60% or greater or about 75% or greater of the dosage form.

In certain preferred embodiments, the controlled release oral dosage form comprises at least one drug which is sparingly soluble to insoluble, at least one polymer having a viscosity less than 50 cps, at least on polymer having a viscosity greater than 200 cps, and the dosage form providing a therapeutic effect for at least 12 hours, wherein each polymer is independently present in an amount less than about 5% or more than about 50%. In certain embodiments the polymer having a viscosity less than 50 cps is present in an amount more than 50%. Preferably, the polymer having a viscosity less than 50 cps is present in an amount less than 5% and the polymer having a viscosity greater than 200 cps is present in an amount more than 50%.

The low viscosity polymers of the present invention preferably have a viscosity of less than 50 cps, e.g., less than about 25 cps, less than about 15 cps, less than about 10 cps or less than about 5 cps. In certain embodiments the polymer having a viscosity less than 50 cps is hydroxypropyl cellulose or hydroxypropylmethylcellulose.

The high viscosity polymers of the present invention preferably have a viscosity of greater than 200 cps, e.g., 1,000 cps or greater, 10,000 cps or greater or 100,000 cps or greater. In certain embodiments the polymer having a viscosity less than 50 cps is hydroxypropyl cellulose or hydroxypropylmethylcellulose.

In certain embodiments of the present invention, when the dosage form is administered in the fed state, there is less than about a 20% increase or decrease, preferably less than about a 10% increase or decrease, in the value for the area under the curve (i.e., AUC)-relative to when the dosage form is administered in the fasted state.

In certain embodiments of the present invention, there is less than about a 50% increase or decrease and preferably less that about 40% increase or decrease in the value for the maximum blood plasma levels of active drug (i.e., $C_{max}$) relative to when the dosage form is administered in the fasted state.

In certain embodiments of the present invention, there is less than about a 40% increase or decrease, preferably less than about a 20% increase or decrease, and most preferably less than about a 10% increase in the time to maximum blood plasma concentration of active drug (i.e., $T_{max}$) relative to when the dosage form is administered in the fasted state.

In certain embodiments of the invention, after oral administration, the composition induces a lower mean fluctuation index in the plasma than an immediate release composition of the drug while maintaining bioavailability substantially equivalent to that of an immediate release composition of the drug (e.g., an erythromycin derivative).

In certain embodiments of the invention, maximum peak concentrations of the drug (e.g., erythromycin derivative) are lower than those produced by an immediate release pharmaceutical composition, and area under the concentration-time curve and the minimum plasma concentration are substantially equivalent to that of the immediate release pharmaceutical composition.

In certain embodiments, the controlled release dosage form is prepared by granulating at least one drug which is sparingly soluble to insoluble with at least one polymer having a viscosity less than 50 cps together with at least one polymer having a viscosity greater than 200 cps; and compressing the granules into a tablet(s) or caplet(s), or placing the granules inside a capsule(s). Alternatively, the controlled release dosage form is prepared by granulating a portion of at least one drug which is sparingly soluble to insoluble with at least one polymer having a viscosity less than 50 cps, and granulating the remaining portion of the at least one drug which is sparing soluble to insoluble with at lease one polymer having a viscosity greater than 200 cps, combining the two granulations to form a mixture, and compressing the mixture into a tablet(s) or caplet(s), or placing the mixture inside a capsule.

In certain embodiments, the controlled release dosage form is prepared by granulating at least one drug which is sparingly soluble to insoluble with at least one polymer having a viscosity less than 50 cps and combining said granules with at least one polymer having a viscosity greater than 200 cps forming a mixture; and compressing the mixture into a tablet(s) or caplet(s), or placing the mixture inside a capsule(s). Alternatively, the controlled release dosage form is prepared by granulating at least one drug which is sparingly soluble to insoluble with at least one polymer having a viscosity greater than 200 cps and combining said granules with at least one polymer having a viscosity less than 50 cps forming a mixture; and compressing the mixture into a tablet(s) or caplet(s), or placing the mixture inside a capsule(s).

The pharmaceutically acceptable polymers useful in the present invention include but are not limited to hydroxypropyl cellulose, hydroxypropylmethyl cellulose, methylcellulose, vinyl acetate/crotonic acid copolymers, maleic anhydride/methyl vinyl ether copolymers, polyalkylene oxide including but not limited to poly(ethylene) oxide, poly(methylene oxide), poly(butylene oxide); poly(hydroxy alkyl methacrylate); poly(vinyl)alcohol, having a low acetal residue, which is cross-linked with glyoxal, formaldehyde or glutaraldehyde and having a degree of polymerization of from 200 to 30,000; a mixture of methyl cellulose, cross-linked agar and carboxymethyl cellulose; a hydrogel forming copolymer produced by forming a dispersion of a finely divided copolymer of maleic anhydride with styrene, ethylene, propylene, butylene or isobutylene cross-linked with from 0.001 to 0.5 moles of saturated cross-linking agent per mole of maleic anyhydride in the copolymer; Carbopol® acidic carboxy polymers having a molecular weight of 450,000 to 4,000,000; Cyanamer® polyacrylamides; cross-linked water swellable indenemaleic anhydride polymers; Goodrite® polyacrylic acid having a molecular weight of 80,000 to 200,000; starch graft copolymers; Aqua-Keeps® acrylate polymer polysaccharides composed of condensed glucose units such as diester cross-linked polyglucan and the like. Other polymers which form hydrogels are described in U.S. Pat. No. 3,865,108; U.S. Pat. No. 4,002,173 and U.S. Pat. No. 4,207,893 all of which are incorporated by reference. Mixtures of the aforementioned pharmaceutically acceptable polymers may also be used. In certain preferred embodiments, the pharmaceutically acceptable polymer is capable of forming a hydrogel. In certain preferred embodiments the pharmaceutically acceptable polymer in combination with the drug is capable of forming a drug matrix for the controlled delivery of the drug.

In a preferred embodiment, the pharmaceutically acceptable polymer or hydrogel is hydroxypropylmethylcellulose, hydroxypropylcellulose, or mixtures thereof. The dosage form may comprise the same polymer having different viscosities and/or different molecular weights. For example, the at least one pharmaceutically acceptable polymer may comprise two hydroxypropylmethylcellulose polymers such as for example Methocel K3 LV (which has a viscosity of about 3 cps) and Methocel K100M CR (which has a viscosity of about 100,000 cps). In addition, the polymer may comprise two hydroxypropylcellulose forms such as Klucel LF and Klucel EF. In addition, the at least one polymer may comprise a mixture of a Klucel and a Methocel.

The polymer preferably forms a viscous gel in water or other solvent system at a sufficient concentration to control the release of the drug.

In certain embodiments, a lubricant, e.g., glyceryl monostearate, may be added prior to blending the two granulations.

In preparing the granulations, a binder may be employed in the present invention in a sufficient amount so that when it is combined with a suitable solvent (e.g., water), granules will be formed which may be compressed into a tablet core. Examples of binders are acacia, cellulose derivatives (such as methylcellulose and carboxymethylcellulose, hydroxypropylmethylcellulose, hydroxypropylcellulose, hydroxyethylcellulose), gelatin, glucose, dextrose, xylitol, polymethacrylates, polyvinylpyrrolidone, starch paste, sucrose, sorbitol, pregelatinized starch, gum tragacanth, alginic acids and salts thereof such as sodium alginate, magnesium aluminum silicate, polyethylene glycol, guar gum, bentonites, and the like.

Prior to compressing the granules, the conventional solid pharmaceutical diluents such as microcrystalline cellulose, lactose, dextrose and the like may be added to the mixture of granulations in amounts from about 0 to 60% weight based on the weight of the compressed, uncoated tablet.

In the preparation of the tablets of the invention, various solvents may be used to prepare the granules. In addition, various other diluents, excipients, lubricants, dyes, pigments, flavorants, colorants, dispersants, emulsifiers, glidants, plasticizers, etc. may be used to optimize the formulations of the invention. The quantities of these additional materials will be sufficient to provide the desired effect to the desired formulation. Specific examples of pharmaceutically acceptable carriers and excipients that may be used to formulate oral dosage forms are described in the *Handbook of Pharmaceutical Excipients*, American Pharmaceutical Association (1986), incorporated by reference herein.

Examples of lubricants are magnesium stearate, glyceryl monostearate, stearic acid, glycerylbehenate, polyethylene glycol, ethylene oxide polymers (for example, available under the registered trademark Carbowax from Union Carbide, Inc., Danbury, Conn.), sodium lauryl sulfate, magnesium lauryl sulfate, sodium oleate, sodium stearyl fumarate, DL-leucine, colloidal silica, and others as known in the art. The lubricant will be in the range of 0 to about 4 percent, and preferably 0 to about 2.5 percent by weight of the compressed, uncoated tablet.

Examples of some disintegrants for use in the present invention are croscarmellose sodium, crospovidone, alginic acid, sodium alginate, methacrylic acid DVB, cross-linked PVP, microcrystalline cellulose, polacrilin potassium, sodium starch glycolate, starch, pregelatinized starch and the like. Some preferable disintegrants are cross-linked polyvinylpyrrolidone (e.g. Kollidon CL), cross-linked sodium carboxymethylcellulose (e.g. Ac-Di-Sol), starch or starch derivatives such as sodium starch glycolate (e.g. Explotab®), or combinations with starch (e.g. Primojel), swellable ion-exchange resins, such as Amberlite IRP 88, formaldehydcasein (e.g. Esma Spreng). Most preferably the disintegrant is sodium starch glycolate. The disintegrant may comprise approximately 0 to about 20% of the total weight of the tablet.

Flavors incorporated in the composition may be chosen from synthetic flavor oils and flavoring aromatics and/or natural oils, extracts from plants leaves, flowers, fruits, and so forth and combinations thereof. These may include cinnamon oil, oil of wintergreen, peppermint oils, clove oil, bay oil, anise oil, eucalyptus, thyme oil, cedar leaf oil, oil of nutmeg, oil of sage, oil of bitter almonds, and cassia oil. Also useful as flavors are vanilla, citrus oil, including lemon, orange, grape, lime and grapefruit, and fruit essences, including apple, banana, pear, peach, strawberry, raspberry, cherry, plum, pineapple, apricot, and so forth. The amount of flavoring may depend on a number of factors including the organoleptic effect desired. Generally, the flavoring will be present in an amount of from 0 to about 2% by weight based on the total tablet weight, when a flavor is used.

Colorants may include titanium dioxide and/or dyes suitable for food such as those known as F. D. & C. dyes and natural coloring agents such as grape skin extract, beet red powder, beta carotene, annato, carmine, turmeric, paprika, and so forth.

Specifically, a protective first coating may be used at a level in the range of from 0 to about 10% by weight which may be applied from a coating system such as opadry Clear sold by Colorcon Corporation. In an especially preferred embodiment, the Opadry Clear will be about 2.83% by weight and will be combined with an osmotic agent in the range of from 0 to about 10% by weight. While the osmotic agent may be any salt, low molecular weight molecule or Water soluble polymers, the preferred agent is sodium chloride. The osmotic agent is added to the coating system when the coating system is being dispersed into purified water. The coating system which contains the osmotic agent may then be sprayed onto the tablets to form a protective coating layer. As mentioned above, this protective first coating is optional.

An optional inner or over coat over the outer coat may also be applied which comprises a pH sensitive polymer which functions as an enteric polymer in that it does not begin to dissolve until pH conditions in excess of the stomach region are encountered. Generally, the pH sensitive materials do not dissolve and begin to release the active drug until a pH above 3.0 and preferably above 5.5. Materials such as such as Eudragit L (copolymer of poly(methacrylic acid, methylmethacrylate), 1:1 ratio; MW No. Av. 135,000 USP Type A) or Eudragit S (copolymer of poly(methacrylic acid, methylmethacrylate), 1:2 ratio MW; No. Av. 135,000-USP Type B) hydroxypropyl methyl cellulose phthalate, cellulose acetate phthalate, polyvinyl acetate phthalate and the like may be used in the range of from 0 to about 30% by weight and preferably from 0 to about 4% by weight of the combined weight of the compressed, uncoated tablet and the inner coating of the pH sensitive polymer.

The following examples illustrate various aspects of the present invention. They are not to be construed to limit the claims in any manner whatsoever.

EXAMPLE 1

A bigranular controlled release tablet containing 500 mg of clarithromycin and having the following formula was prepared. The first granulation (ER1) was prepared with Clarithromycin, USP and one form of Hydroxypropyl Methylcellulose (Methocel K3LV) which were weighed, and wet granulated with isopropyl alcohol/water (9:1) in a vertical granulator. The first granular formulation is shown in Table 1 below:

TABLE 1

| INGREDIENTS | % | kg |
|---|---|---|
| Clarithromycin Granules (ER 1) | | |
| Clarithromycin, USP | 44.00 | 0.440 |
| Hydroxypropyl Methylcellulose, USP | 56.00 | 0.560 |
| (Methocel K3 LV) | | |
| Isopropyl Alcohol, USP | | 0.540 |
| Water | | 0.060 |
| Total: | 100.00 | 1.000 |

The second granulation (ER2) was prepared with Clarithromycin, USP and two forms of Hydroxypropyl Methylcellulose (Methocel K3LV and Methocel K100M CR)

which were weighed, and wet granulated with isopropyl alcohol/water (9:1) in a vertical granulator. The second granular formulation is shown in Table 2 below:

TABLE 2

| Clarithromycin Granules (ER 2): | | |
|---|---|---|
| Clarithromycin, USP | 44.00 | 0.440 |
| Hydroxypropyl Methylcellulose, USP (Methocel K3 LV) | 52.00 | 0.520 |
| Hydroxypropyl Methylcellulose, USP (Methocel K100M CR) | 4.00 | 0.040 |
| Isopropyl Alcohol, USP | * | 0.540 |
| Water | * | 0.060 |
| Total: | 100.00 | 1.000 |

The two granulations were separately weighed and blended in certain amounts along with glyceryl monostearate to formulate a bigranular preparation which was then compressed into tablets using a tableting press as shown in Table 3 below:

TABLE 3

| Clarithromycin Extended Release Tablets, 500 mg | | |
|---|---|---|
| Clarithromycin Granules (ER 1) | 23.64 | 0.1655 |
| Clarithromycin Granules (ER 2) | 74.86 | 0.5240 |
| Glyceryl Monostearate, NF | 1.50 | 0.0105 |
| (Eastman 600P) | | |
| TOTAL | 100.00 | 0.700 |

EXAMPLE 2

A bigranular controlled release tablet containing 500 mg of clarithromycin and having the following formula was prepared as in Example 1 and is shown in Table 4 below:

TABLE 4

| INGREDIENTS | % | kg |
|---|---|---|
| Clarithromycin Granules (ER 1) | | |
| Clarithromycin, USP | 44.00 | 0.440 |
| Hydroxypropyl Methylcellulose, USP (Methocel K3 LV) | 56.00 | 0.560 |
| Isopropyl Alcohol, USP | * | 0.540 |
| Water | * | 0.060 |
| Total: | 100.00 | 1.000 |
| Clarithromycin Granules (ER 2): | | |
| (Clarithromycin, USP | 44.00 | 0.440 |
| Hydroxypropyl Methylcellulose, USP (Methocel K3 LV) | 52.00 | 0.520 |
| Hydroxypropyl Methylcellulose, USP (Methocel K100M CR) | 4.00 | 0.040 |
| Isopropyl Alcohol, USP | * | 0.540 |
| Water | * | 0.060 |
| Total: | 100.00 | 1.000 |
| Clarithromycin Extended Release Tablets, 500 mg | | |
| Clarithromycin Granules (ER 1) | 88.65 | 0.6206 |
| Clarithromycin Granules (ER 2) | 9.85 | 0.0690 |
| Glyceryl Monostearate, NF | 1.50 | 0.0105 |
| (Eastman 600P) | | |
| TOTAL | 100.00 | 0.700 |

In order to test whether a particular erythromycin derivative dosage form exhibits a significant food effect, the most reliable method is actually to test the dosage form in vivo on a subject population, administering the doses in a fed and a fasted state, determine the level of serum (or plasma) drug level with time, plot curves for the concentration of serum (or plasma) drug with time (fed and fasted) as described above, and determine the area under each curve.

Table 5 provides mean plasma pharmacokinetic values based on fasting and non-fasting dosing with Examples 1 and 2 and an equivalent dose of a reference standard (Biaxin XL).

TABLE 5

Comparison of Bioavailability Data of Example 1 and 2 and Reference Standard (Biaxin XL) in fasting and non-fasting state.

| Formulation | Cmax (µg/mL) | Tmax (h) | AUC0-48 (µg · h/ml) |
|---|---|---|---|
| Fasting | | | |
| Example 1 | 1.17 ± 0.46 | 5.6 ± 2.1 | 13.7 ± 5.1 |
| Example 2 | 1.14 ± 0.32 | 4.3 ± 1.6 | 14.7 ± 4.8 |
| Reference Std. (Biaxin XL) | 0.62 ± 0.15 | 6.9 ± 2.7 | 10.0 ± 3.3 |
| Non-Fasting | | | |
| Example 1 | 1.61 ± 0.45 | 5.3 ± 3.5 | 12.8 ± 4.8 |
| Example 2 | 1.85 ± 0.34 | 4.4 ± 1.9 | 13.8 ± 3.8 |
| Reference Std. (Biaxin XL) | 1.3 ± 0.34 | 3.8 ± 1.5 | 12.8 ± 3.5 |

The data in Table 5 show that there is only a small difference in the maximum serum concentration of clarithromycin administered to either a fasting patient or a non-fasting patient by means of Example 1 or 2. Moreover, there is only a 0.3 and 0.1 hour difference in the time required to reach maximum serum concentration of clarithromycin administered by means of Example 1 and Example 2 respectively of the present invention.

However, when clarithromycin is administered by means of the prior art tablet formulation (the reference standard (Biaxin XL)), there is an observable difference in the maximum serum concentration when administered to a non-fasting patient versus administration to a fasting patient. In this case, under the test conditions, there is a significant difference in the time required for the non-fasting dose of clarithromycin to reach maximum serum concentration as opposed to the fasting dose. This "food effect" difference between the prior art (Biaxin XL) tablet formulation for clarithromycin is surprising and appears to be the result of the formulation.

In alternative embodiments of the present invention, the controlled release dosage form comprises a drug having a solubility of less than about 1 part drug in 30 parts water and at least two polymers preferably having different viscosities. Examples of Polymers useful in the dosage form optionally include but are not limited to the pharmaceutically acceptable polymers previously mentioned. Additionally, the dosage form may also comprise any of the previously mentioned binders, diluents, excipients, lubricants, dyes, pigments, flavorants, colorants, dispersants, disintegrants, and emulsifiers. Preferably the at least two polymers have different viscosities and are in different weight percentages. Most preferably the at least two polymers have a viscosity of less than 50 cps, or greater than 200 cps and the polymers. Further it is preferred that the polymers are in an amount of less than 5% w/w or greater than 50% w/w of the total tablet weight. In certain embodiments, the dosage form may be optionally prepared by dry blending the ingredients, or by a singular granulation approach. As mentioned above, the water swellable polymer is preferably hydroxypropylmethylcellulose, hydroxypropylcellulose, or mixtures thereof. The at least two pharmaceutically acceptable polymers may comprise different types of the same polymer, having different viscosities and/or different molecular weights. For example, the two polymers may be two hydroxypropylmethylcellulose forms such as for example Methocel K3 LV (which has a viscosity of about 3 cps) and Methocel K100M CR (which has a viscosity of about 100,000 cps). In addition, the polymers may be two hydroxypropylcellulose forms such as Klucel LF (having a viscosity of and Klucel EF. In addition, the at least polymer may be a mixture of Klucel and Methocel.

Preferably the dosage form provides a mean time to maximum plasma concentration ($T_{max}$) of the drug at from about 1 hour to about 12 hours after administration, preferably at from about 2 to about 10 hours after administration, and most preferably at from about 2 to about 8 hours after administration.

The following Examples are examples of various aspects of the present invention, and are prepared by dry blending all the ingredients except Magnesium Stearate, and thereafter blending the dry blend with Magnesium Stearate. The resulting mixture is then compressed into tablets. Alternatively, the following Examples are prepared by blending all the ingredients except Magnesium Stearate. The blend is then granulated with IPA/water (9:1). The granules are thereafter blended with Magnesium Stearate and compressed into tablets. These Examples are not to be construed to limit the claims in any manner whatsoever.

EXAMPLE 3

A controlled release tablet containing 500 mg of metronidazole and having the formula of Table 6 was prepared as follows:

TABLE 6

| Ingredient | mg/tablet | percent of tablet | Wt.(g) |
| --- | --- | --- | --- |
| Metronidazole | 500.00 | 44 | 22.00 |
| Methocel K3LV | 630.68 | 55.5 | 27.75 |
| Methocel K100M | 0.00 | 0 | 0.00 |
| Magnesium Stearate, NF | 5.68 | 0.5 | 0.25 |
| Total | 1136.36 | 100 | 50.00 |

Manufacturing Procedures:

Dry Blend Approach:
(1) Blend all the ingredients except Magnesium Stearate, then blend with Magnesium Stearate;
(2) Compress the blend into tablets.

Singular Granular Approach:
(1) Blend all the ingredients except Magnesium Stearate, then granulate with IPA/water (9:1);
(2) Blend the granules with Magnesium Stearate and compress the blend into tablets.

EXAMPLE 4

A controlled release tablet containing 500 mg of metronidazole and having the formula of Table 7 was prepared using two polymers having different viscosities and the same manufacturing steps as in Example 3:

TABLE 7

| Ingredient | mg/tablet | percent of tablet | Wt.(g) |
| --- | --- | --- | --- |
| Metronidazole | 500.00 | 44.0 | 22.00 |
| Methocel K3LV | 602.27 | 53.0 | 26.50 |
| Methocel K100M | 28.41 | 2.5 | 1.25 |
| Magnesium Stearate, NF | 5.68 | 0.5 | 0.25 |
| Total | 1136.36 | 100.0 | 50.00 |

EXAMPLE 5

A controlled release tablet containing 500 mg of metronidazole and having the formula of Table 8 was prepared using two polymers having different viscosities and the same manufacturing steps as in Example 3:

TABLE 8

| Ingredient | mg/tablet | percent of tablet | Wt.(g) |
| --- | --- | --- | --- |
| Metronidazole | 500.00 | 44.0 | 22.00 |
| Methocel E15LV | 596.59 | 52.5 | 26.25 |
| Klucel LF | — | — | — |
| Methocel K3 LV | 34.09 | 3.0 | 1.50 |
| Klucel EF | — | — | — |
| Magnesium Stearate, NF | 5.68 | 0.5 | 0.25 |
| Total | 1136.36 | 100.0 | 50.00 |

EXAMPLE 6

A controlled release tablet containing 500 mg of metronidazole and having the formula of Table 9 was prepared using two polymers having different viscosities and the same manufacturing steps as in Example 3:

TABLE 9

| Ingredient | mg/tablet | percent of tablet | Wt.(g) |
| --- | --- | --- | --- |
| Metronidazole | 500.00 | 44.0 | 22.00 |
| Methocel E15LV | — | — | — |
| Klucel LF | 596.59 | 52.5 | 26.25 |
| Methocel K3 LV | 34.09 | 3.0 | 1.50 |
| Klucel EF | — | — | — |
| Magnesium Stearate, NF | 5.68 | 0.5 | 0.25 |
| Total | 1136.36 | 100.0 | 50.00 |

EXAMPLE 7

A controlled release tablet containing 500 mg of metronidazole and having the formula of Table 10 was prepared using two polymers having different viscosities and the same manufacturing steps as in Example 3:

TABLE 10

| Ingredient | mg/tablet | percent of tablet | Wt.(g) |
| --- | --- | --- | --- |
| Metronidazole | 500.00 | 44.0 | 22.00 |
| Methocel E15LV | — | — | — |
| Klucel LF | 596.59 | 52.5 | 26.25 |
| Methocel K3 LV | — | — | — |
| Klucel EF | 34.09 | 3.0 | 1.50 |
| Magnesium Stearate, NF | 5.68 | 0.5 | 0.25 |
| Total | 1136.36 | 100.0 | 50.00 |

While certain preferred and alternative embodiments of the invention have been set forth for purposes of disclosing the invention, modifications to the disclosed embodiments may occur to those who are skilled in the art. Accordingly, the appended claims are intended to cover all embodiments of the invention and modifications thereof which do not depart from the spirit and scope of the invention.

What is claimed is:

1. A controlled release dosage form comprising:
   a. at least one drug which is clarithromycin,
   b. at least one polymer, having a viscosity less than 50 cps wherein the polymer having viscosity less than 50 cps is hydroxypropyl cellulose or hydroxypropyl methylcellulose wherein said polymer having a viscosity less than 50 cps is present in an amount more than 50% based on the weight of the dosage form, and
   c. at least one polymer, having a viscosity greater than 200 cps wherein the polymer having viscosity greater than 200 cps is hydroxypropyl cellulose or hydroxypropyl methylcellulose; said dosage form providing a therapeutic effect for at least 12 hours and wherein the maximum blood plasma concentration of the active drug (Cmax) when said dosage form is administered to a patient in a fed state is less than 50% higher or lower than the Cmax of said dosage form when administered in the fasted state, the area under the curve (AUC) when said dosage form is administered to a patient in a fed state in less than 20% higher or lower than the AUC of said dosage form when administered in the fasted state and the time to maximum blood plasma concentration (Tmax) when said dosage form is administered to a patient in a fed state is less than about 20% higher or lower than the Tmax of said dosage form when administered in the fasted state.

2. The controlled release dosage form of claim 1 wherein said dosage form does not exhibit an in vivo food effect.

3. The controlled release dosage form of claim 1 wherein maximum blood plasma concentration of active drug (Cmax) administered in a fed state is less than 40% higher or lower than Cmax of said dosage form administered in the fasted state.

4. The controlled release dosage form of claim 1 wherein the area under the curve (AUC) when administered in a fed state is less that 10% higher or lower than the AUC of said dosage form administered in the fasted state.

5. The controlled release dosage form of claim 1 wherein said polymer having a viscosity less than 50 cps, further has a viscosity less than about 15 cps.

6. The controlled release dosage form of claim 1 wherein said polymer having a viscosity less than 50 cps, further has a viscosity less than about 5 cps.

7. The controlled release dosage form of claim 1 wherein said polymer with a viscosity greater than 200 cps further has a viscosity greater than about 1000 cps.

8. The controlled release dosage form of claim 1 wherein said polymer with a viscosity greater than 200 cps further has a viscosity greater than about 10,000 cps.

9. The controlled release dosage form of claim 1 wherein said polymer having a viscosity greater than 200 cps further has a viscosity greater than about 100,000 cps.

10. The controlled release dosage form of claim 1 comprising a drug granulate formed by:
    a. granulating said drug with said polymer having a viscosity less than 50 cps together with said polymer having a viscosity greater than 200 cps; and
    b. compressing said granules into a tablet or caplet, or placing said granules inside a capsule.

11. The controlled release dosage form of claim 1 comprising a drug granulate formed by:
    a. granulating said drug with said polymer having viscosity less than 50 cps,
    b. combining said granules with said polymer having viscosity greater than 200 cps to form a mixture; and
    c. compressing said mixture into a tablet or caplet, or placing said mixture inside a capsule.

12. The controlled release dosage form of claim 1 comprising a drug granulate formed by:
    a. granulating said drug with said polymer having viscosity greater than 200 cps,
    b. combining said granules with said polymer having viscosity less than 50 cps to form a mixture; and
    c. compressing said mixture into a tablet or caplet, or placing said granules inside a capsule.

13. The controlled release dosage form of claim 1 comprising a drug granulate formed by:
    a. granulating a portion of said drug with said polymer having viscosity less than 50 cps,
    b. granulating the remaining portion of said drug with said polymer having a viscosity greater than 200 cps,
    c. combining the aforementioned granules to form a mixture; and
    d. compressing said mixture into a tablet or caplet, or placing said mixture inside a capsule.

14. The controlled release dosage form of claim 1 wherein the Tmax of the dosage form when administered in a fed state is less than about 10% higher or lower than the Tmax of said dosage form administered in the fasted state.

15. The controlled release dosage form of claim 1 wherein the combined amount of the polymer with a viscosity less than 50 cps and the polymer with a viscosity greater than 200 cps is about 55% or greater based on the weight of the dosage form.

* * * * *